United States Patent [19]

Nadelson

[11] 4,086,421
[45] Apr. 25, 1978

[54] SUBSTITUTED ISOXAZOLO PYRIDINONES
[75] Inventor: Jeffrey Nadelson, Denville, N.J.
[73] Assignee: Sandoz, Inc., E. Hanover, N.J.
[21] Appl. No.: 805,881
[22] Filed: Jun. 13, 1977

Related U.S. Application Data
[62] Division of Ser. No. 705,702, Jul. 15, 1976, Pat. No. 4,049,813.

[51] Int. Cl.² .......................................... C07D 491/04
[52] U.S. Cl. ............................ 544/127; 260/268 BC
[58] Field of Search ................... 544/127; 260/268 BC

[56] References Cited
U.S. PATENT DOCUMENTS
4,049,813  9/1977  Nadelson ..................... 260/296 H

*Primary Examiner*—Henry R. Jiles
*Assistant Examiner*—R. W. Ramsuer
*Attorney, Agent, or Firm*—Gerald D. Sharkin; Robert S. Honor; Timothy G. Rothwell

[57] ABSTRACT

This disclosure describes novel compounds of the formula

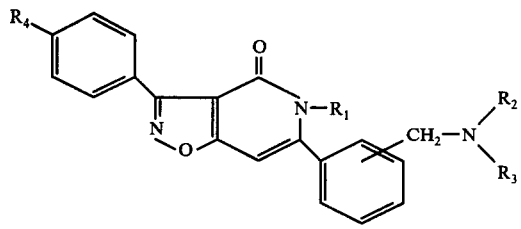

where
R₁ is straight chain lower alkyl, and
R₂ and R₃ independently represent hydrogen or lower alkyl or together with N represent

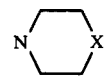

where
X is CH₂, O or N—CH₃, and
R₄ is hydrogen, halo having an atomic weight of about 19 to 36 or lower alkoxy which are useful as hypolipidemic agents.

4 Claims, No Drawings

SUBSTITUTED ISOXAZOLO PYRIDINONES

This is a division of application Ser. No. 705,702, filed July 15, 1976, now U.S. Pat. No. 4,049,813.

This invention relates to substituted isoxazolo pyridinones which exhibit hypolipidemic activity. In particular, it relates to 3-substituted-5-methyl-6-substituted-isoxazolo-[4,5-c]pyridin-4(5H)-ones, intermediates thereof and pharmaceutically acceptable salts.

The compounds of this invention may be represented by the following structural formula

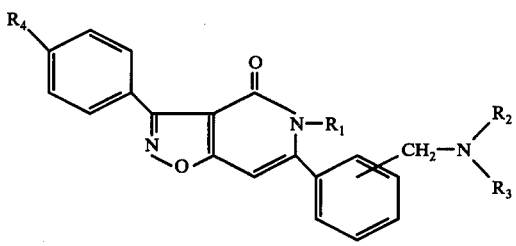
(I)

where

R$_1$ is straight chain lower alkyl, i.e., straight chain lower alkyl having 1 to 4 carbon atoms, e.g., methyl, ethyl, propyl and the like, and R$_2$ and R$_3$ each independently represent hydrogen or lower alkyl, i.e., alkyl having 1 to 4 carbon atoms, e.g., methyl, ethyl, isopropyl and the like, or together with N represent

where

X is CH$_2$, O, or N—CH$_3$, and

R$_4$ is hydrogen, halo having an atomic weight of about 19 to 36 or lower alkoxy, i.e., alkoxy having 1 to 4 carbon atoms, e.g., methoxy, ethoxy, propoxy and the like.

The compounds of formula (I) are prepared according to the following reaction scheme:

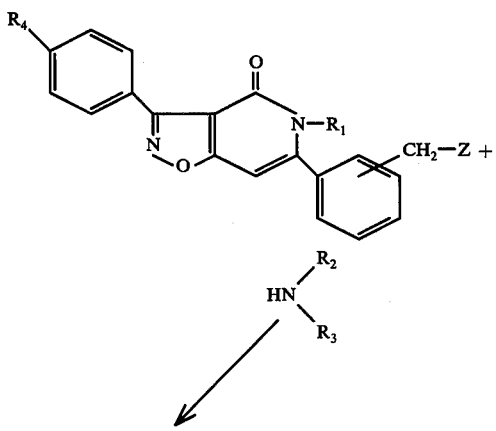

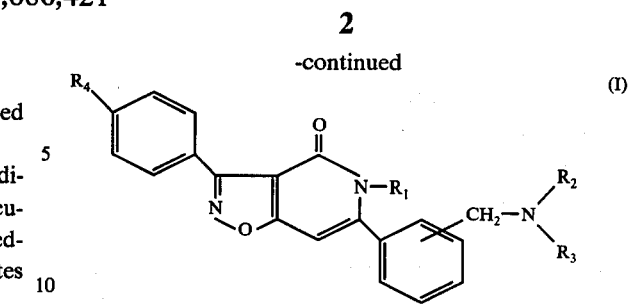
(I)

where

Z represents chlorine or bromine, and

R$_1$, R$_2$, R$_3$ and R$_4$ are as defined above.

The compounds of formula (I) are prepared by reacting a compound of the formula (II) with a compound of the formula (III) in the presence of an inert organic solvent. Although the particular solvent employed is not critical, the preferred solvents include the halogenated hydrocarbons such as methylene dichloride, chloroform, carbon tetrachloride and the like or the aromatic hydrocarbons such as benzene, toluene and the like, preferably toluene. The temperature of the reaction is not critical, but it is preferred that the reaction be run from about 20° to 150° C., preferably from about 30° to 60° C. The reaction is run from about 10 to 30 hours, preferably from about 16 to 24 hours. The product is recovered using conventional techniques, e.g., filtration followed by evaporation.

The compounds of formula (II) are prepared according to the following reaction scheme:

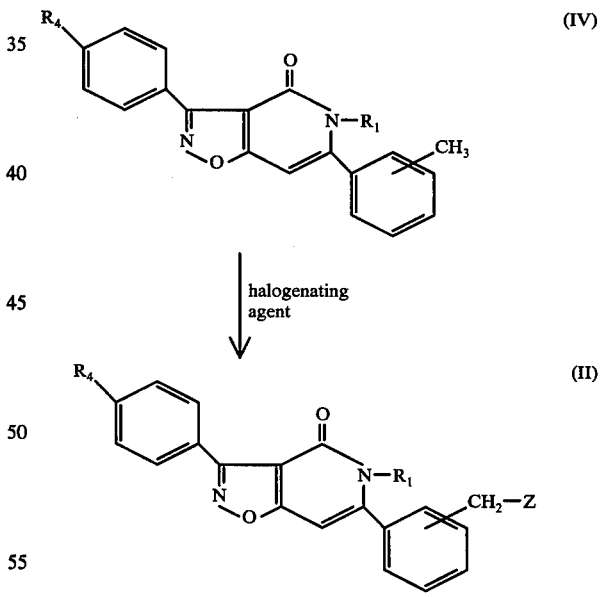

where Z, R$_1$ and R$_4$ are as defined above.

The compounds of formula (II) are prepared by treating a compound of the formula (IV) with a halogenating agent in the presence of an inert organic solvent and free radical initiation. Although the particular halogenating agent employed is not critical, it is preferred that the reaction be run in the presence of chlorine, bromine, N-chlorosuccinimide, N-bromosuccinimide, N-bromo phthalimide, N-bromo-acetamide, and the like, preferably N-bromosuccinimide. In the preferred process, the free radical initiator used is an organic or inorganic peroxide, especially benzoylperoxide. The reaction can also be carried out under ultraviolet light. Although the particular solvent used is not critical, the preferred solvents include the aromatic hydrocarbons such as benzene, toluene and the like or the halogenated hydrocarbons such as methylene dichloride, chloroform or carbon tetrachloride, the latter being especially preferred. The temperature of the reaction is not critical, but it is preferred that the reaction be run from about 60° to 150° C., preferably the reflux temperature of the solvent. The reaction is run from about 1 to 10 hours, preferably from about 2 to 9 hours. The resulting product was identified by NMR analysis.

The compounds of formula (IV) are prepared according to the following reaction scheme:

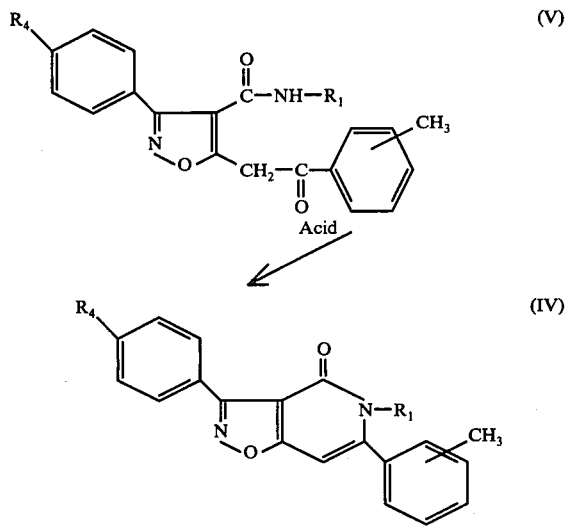

where $R_1$ and $R_4$ are as defined above

The compounds of formula (IV) are prepared by treating a compound of the formula (V) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being especially preferred. The temperature of the reaction is not critical, but it is preferred that the reaction be run from about 80° to 150° C., preferably the reflux temperature of the solvent. The reaction is run from about 12 to 36 hours, preferably from about 20 to 36 hours. The product is recovered using conventional techniques, e.g., trituration followed by recrystallization.

The compounds of formula (V) are prepared according to the following reaction scheme:

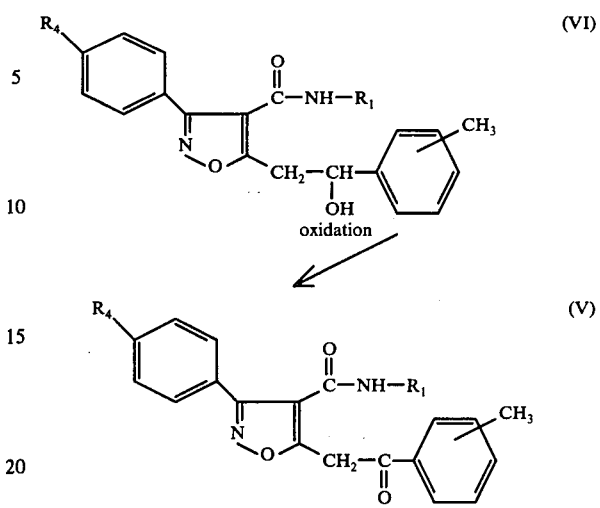

where $R_1$ and $R_4$ are as defined above.

The compounds of formula (V) are prepared by treating a compound of the formula (VI) with an oxidizing agent such as chromium trioxide, potassium permanganate, and the like, preferably chromium trioxide, under acidic conditions in the presence of water and acetone. Although the particular acid employed is not critical, the preferred acids include the mineral acids such as acetic acid, hydrochloric acid or sulfuric acid, the latter being especially preferred. The particular solvent employed is not critical, and depending upon the oxidizing agent utilized above, may include acetone, pyridine and the like, preferably acetone. The temperature of the reaction is not critical, but it is preferred that the reaction be run from about 0° to 50° C., preferably from about 20° to 30° C. The reaction is run from about 1 to 10 hours, preferably from about 2 to 4 hours. The product is recovered using conventional techniques, e.g., trituration followed by filtration.

The compounds of formula (VI) are prepared according to the following reaction scheme:

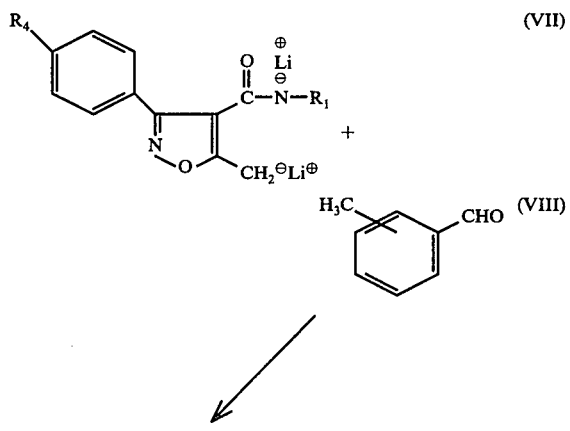

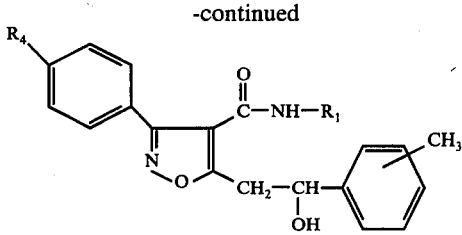

(VI)

where $R_1$ and $R_4$ are as defined above.

The compounds of formula (VI) are prepared by treating a compound of the formula (VII) with a compound of the formula (VIII) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably tetrahydrofuran. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product is recovered using conventional techniques, e.g., trituration followed by filtration.

The compounds of formula (VII) are prepared according to the following reaction scheme:

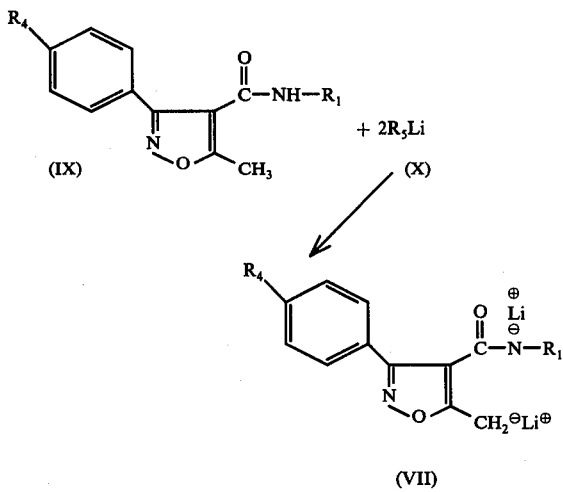

where
$R_5$ is lower alkyl having 1 to 4 carbon atoms, and
$R_1$ and $R_4$ are as defined above.

The compounds of formula (VII) are prepared by treating a compound of the formula (IX) with a compound of the formula (X) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably hexane. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The compound of formula (VII) is not isolated but employed in situ as a starting material in the preparation of the compounds of formula (VI).

Many of the compounds of formulae (III), (VIII), (IX) and (X) are known and may be prepared by methods described in the literature. The compounds of formulae (III), (VIII), (IX) and (X) not specifically described may be prepared by analogous methods from known starting materials.

The compounds of formula (I) are useful because they possess pharmaceutical activity in animals as hypolipidemic agents, as indicated by the fall in cholesterol and triglyceride levels in male albino Wistar rats weighing 110–130 g. initially. The rats are maintained on drug-free laboratory chow diet for 7 days and then divided into groups of 8 to 10 animals. Each group with the exception of the control is then given orally 120 milligrams per kilogram of body weight per diem of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, [345-347]) are added, and the mixture is shaken for 1 hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like.

The hypolipidemic effective dosage of these active compounds in the alleviation of lipidemia may vary depending on the particular compound employed and the severity of the condition being treated. However, in general, satisfactory results are obtained when the compounds of formula (I) are administered at a daily dosage of from about 4.0 milligrams to about 250 milligrams per kilogram of animal body weight, preferably given in divided doses two to four times a day, or in sustained release form. For most large mammals, the total daily dosage is from about 250 milligrams to about 1000 milligrams. Dosage forms suitable for internal use comprise from about 62.5 to about 500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
| --- | --- |
| 5-methyl-3-phenyl-6-(p-[dimethyl-aminomethyl]phenyl)-isoxazolo [4,5-c]pyridin-4(5H)-one | 150 |
| inert solid diluent (starch, lactose, kaolin) | 300 |

EXAMPLE 1

3-Phenyl-5-(4-methyl-$\beta$-hydroxyphenethyl)-N-methyl-isoxazole-4-carboxamide

A suspension of 75 g. (0.348 mole) of 3-phenyl-5,N-dimethyl-isoxazole-4-carboxamide and 1 liter of tetrahydrofuran is cooled to $-65°$ C. and 478 ml. of 1.6M n-butyllithium in hexane (0.765 mole) is added dropwise maintaining the temperature between $-60°$ and $-70°$ C. After the addition is complete, the orange suspension is stirred for 1½ hours at $-60°$ to $-70°$ C., and then 37.2 g. (0.350 mole) of p-tolualdehyde in 375 ml. tetrahydrofuran is added dropwise maintaining the temperature between $-60°$ and $-70°$ C. After addition is complete the mixture is stirred for 1½ hrs. at $-60°$ to $-70°$ C. and then warmed to $-30°$ C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered and evaporated in vacuo. The solid residue is triturated with a 50:50 mixture of ether:petroleum ether, filtered and washed with cold ether to give 3-phenyl-5-(4-methyl-$\beta$-hydroxyphenethyl)-N-methyl-isoxazole-4-carboxamide; m.p. 148° to 150° C.

Following the above procedure and using in place of 3-phenyl-5,N-dimethyl-isoxazole-4-carboxamide an equivalent amount of a. 3-(p-chlorophenyl)-5,N-dimethyl-isoxazole-4-carboxamide,
b. 3-(p-fluorophenyl)-5,N-dimethyl-isoxazole-4-carboxamide,
c. 3-(p-anisyl)-5,N-dimethyl-isoxazole-4-carboxamide there is obtained a. 3-(p-chlorophenyl)-5-(4-methyl-$\beta$-hydroxyphenethyl)-N-methyl-isoxazole-4-carboxamide,
b. 3-(p-fluorophenyl)-5-(4-methyl-$\beta$-hydroxyphenethyl)-N-methyl-isoxazole-4-carboxamide, or
c. 3-(p-anisyl)-5-(4-methyl-$\beta$-hydroxyphenethyl)-N-methyl-isoxazole-4-carboxamide, respectively.

Again following the above procedure but using in place of p-tolualdehyde, an equivalent amount of d. o-tolualdehyde or
e. m-tolualdehyde there is obtained d. 3-phenyl-5-(2-methyl-$\beta$-hydroxyphenethyl)-N-methyl-isoxazole-4-carboxamide or
e. 3-phenyl-5-(3-methyl-$\beta$-hydroxyphenethyl)-N-methyl-isoxazole-4-carboxamide, respectively.

EXAMPLE 2

N-methyl-5-(4-methylphenacyl)-3-phenyl-4-isoxazole carboxamide

A mixture of 41.4 g. (0.123 mole) of 3-phenyl-5-(4-methyl-$\beta$-hydroxyphenethyl)-N-methyl-isoxazole-4-carboxamide and 800 ml. of acetone is treated dropwise with the addition of 92.5 ml. (0.185 mole) of Jones reagent [100 g. chromium trioxide, 160 ml. concentrated sulfuric acid with water to 500 ml.] and the resulting mixture is stirred at room temperature for 2 hours. The supernatant liquid is decanted and the solvent removed in vacuo, the residue is taken up in water/methylene chloride and the layers separated. The organic phase is washed with saturated sodium chloride solution, dried over anhydrous magnesium sulfate, filtered and evaporated in vacuo. The residue is treated with ether to give a solid and then triturated with ethanol to give N-methyl-5-(4-methylphenacyl)-3-phenyl-4-isoxazole carboxamide.

Following the above procedure and using in place of 3-phenyl-5-(4-methyl-$\beta$-hydroxyphenethyl)-N-methyl-isoxazole-4-carboxamide, an equivalent amount of a. 3-(p-chlorophenyl)-5-(4-methyl-$\beta$-hydroxyphenethyl)-N-methyl-isoxazole-4-carboxamide,
b. 3-(p-fluorophenyl)-5-(4-methyl-$\beta$-hydroxyphenethyl)-N-methyl-isoxazole-4-carboxamide,
c. 3-(p-anisyl)-5-(4-methyl-$\beta$-hydroxyphenethyl)-N-methyl-isoxazole-4-carboxamide,
d. 3-phenyl-5-(2-methyl-$\beta$-hydroxyphenethyl)-N-methyl-isoxazole-4-carboxamide, or
e. 3-phenyl-5-(3-methyl-$\beta$-hydroxyphenethyl)-N-methyl-isoxazole-4-carboxamide there is obtained a. N-methyl-5-(4-methylphenacyl)-3-(p-chlorophenyl)-4-isoxazole carboxamide,
b. N-methyl-5-(4-methylphenacyl)-3-(p-fluorophenyl)-4-isoxazole carboxamide,
c. N-methyl-5-(4-methylphenacyl)-3-(p-anisyl)-4-isoxazole carboxamide,
d. N-methyl-5-(2-methylphenacyl)-3-phenyl-4-isoxazole carboxamide, or
e. N-methyl-5-(3-methylphenacyl)-3-phenyl-4-isoxazole carboxamide, respectively.

EXAMPLE 3

5-Methyl-3-phenyl-6-(p-tolyl)-isoxazolo[4,5-c]pyridin-4(5H)-one

A mixture of 26.1 g. (0.0815 mole) of N-methyl-5-(4-methylphenacyl)-3-phenyl-4-isoxazole carboxamide and 261 ml. of 2M sulfuric acid is refluxed for 24 hours. The mixture is cooled and extracted with methylene chloride. The methylene chloride layer is washed with water and then brine, dried over anhydrous magnesium sulfate, filtered and evaporated in vacuo. The residue is triturated with ether and then recrystallized from ethanol to give 5-methyl-3-phenyl-6-(p-tolyl)-isoxazolo[4,5-c]pyridin-4(5H)-one; m.p. 155° to 156° C.

Following the above procedure and using in place of N-methyl-5-(4-methylphenacyl)-3-phenyl-4-isoxazole carboxamide, an equivalent amount of a. N-methyl-5-(4-methylphenacyl)-3-(p-chlorophenyl)-4-isoxazole carboxamide,
b. N-methyl-5-(4-methylphenacyl)-3-(p-fluorophenyl)-4-isoxazole carboxamide,
c. N-methyl-5-(4-methylphenacyl)-3-(p-anisyl)-4-isoxazole carboxamide,
d. N-methyl-5-(2-methylphenacyl)-3-phenyl-4-isoxazole carboxamide, or
e. N-methyl-5-(3-methylphenacyl)-3-phenyl-4-isoxazole carboxamide, there is obtained a. 5-methyl-3-(p-chlorophenyl)-6-(p-tolyl)-isoxazolo[4,5-c]pyridin-4(5H)-one,
b. 5-methyl-3-(p-fluorophenyl)-6-(p-tolyl)-isoxazolo[4,5-c]pyridin-4(5H)-one,
c. 5-methyl-3-(p-anisyl)-6-(p-tolyl)-isoxazolo[4,5-c]pyridin-4(5H)-one,
d. 5-methyl-3-phenyl-6-(o-tolyl)-isoxazolo[4,5-c]pyridin-4(5H)-one, or
e. 5-methyl-3-phenyl-6-(m-tolyl)-isoxazolo[4,5-c]pyridin-4(5H)-one, respectively.

EXAMPLE 4

5-Methyl-3-phenyl-6-(p-bromomethylphenyl)-isoxazolo[4,5-c]pyridin-4(5H)-one

A mixture of 34.9 g. (0.110 mole) of 5-methyl-3-phenyl-6-(p-tolyl)-isoxazolo[4,5-c]pyridin-4(5H)-one, 21.6 g. (0.121 mole) N-bromosuccinimide and 0.1 g. benzoyl peroxide in 500 ml. carbon tetrachloride is refluxed for 2 hours. The resulting mixture is cooled and the solid filtered and washed with more carbon tetrachloride. The solvent is then removed in vacuo and the resulting solid is determined by NMR to contain 62% of 5-methyl-3-phenyl-6-(p-bromomethylphenyl)-isoxazolo[4,5-c]pyridin-4(5H)-one.

Following the above procedure and using in place of 5-methyl-3-phenyl-6-(p-tolyl)-isoxazolo[4,5-c]pyridin-4(5H)-one an equivalent amount of a. 5-methyl-3-(p-chlorophenyl)-6-(p-tolyl)-isoxazolo[4,5-c]pyridin-4(5H)-one,
b. 5-methyl-3-(p-fluorophenyl)-6-(p-tolyl)-isoxazolo[4,5-c]pyridin-4(5H)-one,
c. 5-methyl-3-(p-anisyl)-6-(p-tolyl)-isoxazolo[4,5-c]pyridin-4(5H)-one,
d. 5-methyl-3-phenyl-6-(o-tolyl)-isoxazolo[4,5-c]pyridin-4(5H)-one, or
e. 5-methyl-3-phenyl-6-(m-tolyl)-isoxazolo[4,5-c]pyridin-4(5H)-one there is obtained a. 5-methyl-3-(p-chlorophenyl)-6-(p-bromomethylphenyl)-isoxazolo[4,5-c]pyridin-4(5H)-one,
b. 5-methyl-3-(p-fluorophenyl)-6-(p-bromomethylphenyl)-isoxazolo[4,5-c]pyridin-4(5H)-one,
c. 5-methyl-3-(p-anisyl)-6-(p-bromomethylphenyl)-isoxazolo[4,5-c]pyridin-4(5H)-one,
d. 5-methyl-3-phenyl-6-(o-bromomethylphenyl)-isoxazolo[4,5-c]pyridin-4(5H)-one, or
e. 5-methyl-3-phenyl-6-(m-bromomethylphenyl)-isoxazolo[4,5-c]pyridin-4(5H)-one, respectively.

EXAMPLE 5

5-Methyl-3-phenyl-6-(p-[dimethylaminomethyl]phenyl)-isoxazolo[4,5-c]pyridin-4(5H)-one A mixture of 21.2 g. of the product of Example 4, containing 62% of 5-methyl-3-phenyl-6-(p-bromomethylphenyl)-isoxazolo[4,5-c]pyridin-4(5H)-one 0.0332 mole of bromo compound) and 7.2 g. (0.160 mole) dimethylamine in 300 ml. toluene is stirred overnight at room temperature. The mixture is filtered and the solid washed with toluene and the solvent evaporated in vacuo. The resulting solid is dissolved in methylene chloride and treated with 2N hydrochloric acid, the precipitate is then filtered, washed with water and ether. The solid is then dissolved in methylene chloride and 2N sodium dioxide and the organic phases separated and washed with water, dried over anhydrous magnesium sulfate, filtered and evaporated in vacuo to give 5-methyl-3-phenyl-6-(p-[dimethylaminomethyl]phenyl)-isoxazolo[4,5-c]pyridin-4(5H)-one; m.p. 159°–161° C.

Following the above procedure and using in place of 5-methyl-3-phenyl-6-(p-bromomethylphenyl)-isoxazolo[4,5-c]pyridin-4(5H)-one, an equivalent amount of a. 5-methyl-3-(p-chlorophenyl)-6-(p-bromomethylphenyl)-isoxazolo[4,5-c]pyridin-4(5H)-one,
b. 5-methyl-3-(p-fluorophenyl)-6-(p-bromomethylphenyl)-isoxazolo[4,5-c]pyridin-4(5H)-one,
c. 5-methyl-3-(p-anisyl)-6-(p-bromomethylphenyl)-isoxazolo[4,5-c]pyridin-4(5H)-one,
d. 5-methyl-3-phenyl-6-(o-bromomethylphenyl)-isoxazolo[4,5-c]pyridin-4(5H)-one, or
e. 5-methyl-3-phenyl-6-(m-bromomethylphenyl)-isoxazolo[4,5-c]pyridin-4(5H)-one there is obtained a. 5-methyl-3-(p-chlorophenyl)-6-(p-[dimethylaminomethyl]phenyl)-isoxazolo[4,5-c]pyridin-4(5H)-one,
b. 5-methyl-3-(p-fluorophenyl)-6-(p-[dimethylaminomethyl]phenyl)-isoxazolo[4,5-c]pyridin-4(5H)-one,
c. 5-methyl-3-(p-anisyl)-6-(p-[dimethylaminomethyl]phenyl)-isoxazolo[4,5-c]pyridin-4(5H)-one,
d. 5-methyl-3-phenyl-6-(o-[dimethylaminomethyl]phenyl)-isoxazolo[4,5-c]pyridin-4(5H)-one, or
e. 5-methyl-3-phenyl-6-(m-[dimethylaminomethyl]phenyl)-isoxazolo[4,5-c]pyridin-4(5H)-one, respectively.

Again following the above procedure and using in place of dimethylamine an equivalent amount of f. methylamine,
g. N-methyl-piperazine,
h. piperidine, or
i. morpholine there is obtained f. 5-methyl-3-phenyl-6-(p-[methylaminomethyl]phenyl)-isoxazolo[4,5-c]pyridin-4(5H)-one,
g. 5-methyl-3-phenyl-6-(p-[N-methyl-piperazinomethyl]phenyl)-isoxazolo[4,5-c]pyridin-4(5H)-one,
h. 5-methyl-3-phenyl-6-(p-[piperidinomethyl]phenyl)-isoxazolo[4,5-c]pyridin-4(5H)-one, or i. 5-methyl-3-phenyl-6-(p-[morpholinomethyl]phenyl)-isoxazolo[4,5-c]pyridin-4(5H)-one, respectively.

The 5-methyl-3-phenyl-6-(p-[dimethylaminomethyl]phenyl)-isoxazolo[4,5-c]pyridin-4(5H)-one of this example is an effective hypolipidemic agent when orally administered to an animal suffering from lipidemia at a dosage of 150 mg. four times per day.

What is claimed is:

1. A compound of the formula

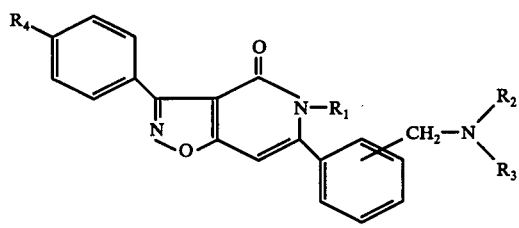

where

R₁ represents straight chain lower alkyl, and

R₂ and R₃ together with N represent

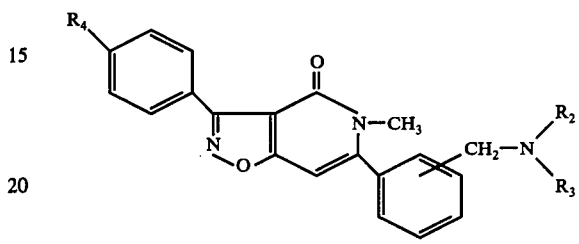

where

X is O or N—CH₃, and

R₄ is hydrogen, halo having an atomic weight of about 19 to 36 or lower alkoxy, or a pharmaceutically acceptable salt thereof.

2. A compound of the formula where R₂, R₃ and R₄ are as defined in claim 1, or a pharmaceutically acceptable salt therof.

3. The compound of claim 1 which is 5-methyl-3-phenyl-6-(p-[morpholinomethyl]phenyl)-isoxazolo[4,5-c]pyridin-4(5H)-one.

4. The compound of claim 1 which is 5-methyl-3-phenyl-6-(p-[N-methyl-piperazinomethyl]phenyl)-isoxazolo[4,5-c]pyridin-4(5H)-one.

* * * * *